(12) United States Patent
Kundu et al.

(10) Patent No.: US 6,656,505 B2
(45) Date of Patent: Dec. 2, 2003

(54) METHOD FOR FORMING AN AQUEOUS FLOCCULATED SUSPENSION

(75) Inventors: Subhas Kundu, Ellicott City, MD (US); Vivek Desai, Ellicott City, MD (US); Andrea Cameron, Baltimore, MD (US)

(73) Assignee: Alpharma USPD Inc., Baltimore, MD (US)

( * ) Notice: Subject to any disclaimer, the term of this patent is extended or adjusted under 35 U.S.C. 154(b) by 349 days.

(21) Appl. No.: 09/621,623

(22) Filed: Jul. 21, 2000

(65) Prior Publication Data

US 2002/146455 A1 Oct. 10, 2002

(51) Int. Cl.⁷ .................. A61K 9/10; A61K 31/56
(52) U.S. Cl. ............... 424/489; 424/722; 514/178
(58) Field of Search ............... 424/489, 722; 514/178

(56) References Cited

U.S. PATENT DOCUMENTS

| | | | |
|---|---|---|---|
| 3,356,573 A | | 12/1967 | Kirk et al. |
| 4,370,321 A | | 1/1983 | Greaney et al. |
| 4,396,615 A | | 8/1983 | Petrow et al. |
| 4,435,524 A | * | 3/1984 | Dinbergs ............... 521/65 |
| 4,666,885 A | | 5/1987 | Labrie |
| 4,702,844 A | | 10/1987 | Flesher et al. |
| 4,760,053 A | | 7/1988 | Labrie |
| 4,775,661 A | | 10/1988 | Labrie |
| 5,112,604 A | | 5/1992 | Beaurline et al. |
| 5,145,684 A | | 9/1992 | Liversidge et al. |
| 5,338,732 A | * | 8/1994 | Atzinger et al. ............ 514/178 |
| 5,712,310 A | | 1/1998 | Koch |
| 6,028,065 A | * | 2/2000 | Ragunathan et al. ....... 514/178 |
| 2002/0028794 A1 | | 3/2002 | Brubaker et al. |

OTHER PUBLICATIONS

Yu CD, Polyoxyethylene Castor Oil Derivatives, Handbook of Pharmaceutical Excipients, pp. 412–415, 3rd Ed., 1995.
The Pharmacological Basis of Therapeutics; Agents Affecting Gastrointestinal Water Flux and Motility (Chap. 38), 1990.
The United States Pharmacopeia, United States Pharacopeial Convention, Inc.; Polyoxyl/Official Monographs, pp. 2500–2501, 2000.

* cited by examiner

Primary Examiner—Thurman K. Page
Assistant Examiner—Rachel M. Bennett
(74) Attorney, Agent, or Firm—Dickstein Shapiro Morin & Oshinsky LLP

(57) ABSTRACT

An aqueous pharmaceutical composition suitable for oral delivery has an insoluble active substance and a wetting agent in liquid suspension. The composition contains floccules of the active ingredient. The formulation has an excellent shelf-life in which caking and sedimentation are inhibited. The composition may be resuspended upon light to moderate shaking.

24 Claims, No Drawings

METHOD FOR FORMING AN AQUEOUS FLOCCULATED SUSPENSION

BACKGROUND OF THE INVENTION

1. Field of the Invention

The present invention relates to aqueous suspensions of active substances, and in particular, to aqueous flocculated suspensions containing one or more insoluble actives which are suitable for oral delivery. The invention also relates to the use of certain surfactants to enhance flocculation in aqueous pharmaceutical suspensions.

2. Background

There have been many attempts to formulate aqueous suspensions of water-insoluble pharmaceutical active ingredients. Flocculated suspensions in particular are desirable in numerous applications. They are well suited for oral delivery of the active, and are often preferred for patients for whom swallowing pills or other dosage forms is difficult. A flocculated suspension contains the active pharmaceutical dispersed throughout the liquid medium. Minute particles of the active agent associate themselves with one or more excipients to form an agglomerated mass which is referred to as a "floccule" or "floc". Other excipients in turn act to suspend the snowflake-like flocs in the water. The goal is to achieve a dispersion in which the active pharmaceutical component can be uniformly suspended and dispersed upon light to moderate shaking. In this way, the patient can be assured of receiving not only the appropriate dosage of the active, but substantially the same dosage upon each administration.

Many surfactants available in the art act as wetting agents for water-insoluble actives. These wetting agents greatly facilitate the formation of aqueous suspensions by reducing the surface tension between the active and the aqueous phase. Other compounds function as suspending agents which maintain the wetted active in uniform dispersion throughout the liquid media. The problem which arises is finding the right combination of compounds which are best suited for the particular active. Another problem is finding the particular concentration range which will enhance flocculation and ensure adequate floccule size. In addition to achieving good dispersion and uniformity, another goal is ensuring the optimal bioavailability of the active. The floccules should permit the active to be absorbed by the body at a rate and in an amount which will facilitate its efficacy. Moreover, the active should be stable in the aqueous suspension over its entire shelf-life.

Atzinger et al., U.S. Pat. No. 5,338,732, is directed to a flocculated suspension containing the active substance megestrol acetate, together with polyethylene glycol and polysorbate, in particular polysorbate 80. The polysorbate component is present in an amount of 0.005% to 0.015%. At polysorbate 80 concentrations as low as 0.025% the patentees note significant deflocculation and caking of the formulation. In addition, Table 4 in the reference shows a significant decrease in physical stability at a concentration of 0.02% polysorbate 80.

Thus, there exists a need in the art to find a suitable combination of compounds which together with one or more pharmaceutical actives can form a stable flocculated liquid suspension. There also exists a need for an improved flocculated suspension containing one or more actives together with a synergistic amount of one or more excipients. There is a further need in the art to avoid the aforementioned issues associated with the use of polyethylene glycol together with polysorbate in forming a megestrol acetate formulation.

SUMMARY OF INVENTION

The invention according to one embodiment is a composition containing at least one insoluble active substance together with at least one wetting agent. The concentration of the wetting agent is sufficient to form a stable, flocculated suspension of the active substance.

Also provided as part of the invention is a method for forming a composition which involves combining at least one active substance and at least one wetting agent, wherein the wetting agent is present in an amount sufficient to form a stable, flocculated suspension of the active substance.

Further provided is a method for forming an aqueous flocculated suspension containing an insoluble active substance together with a wetting agent in which the wetting agent is added in an amount below which the floccule size in the suspension starts to increase.

The invention also provides an oral pharmaceutical composition having about 0.5 to about 10% of megestrol acetate; about 0.01 to about 0.04% of docusate sodium; and about 10 to about 30% of at least one suspending agent.

There is also provided as part of the invention an oral composition having about 1 to about 8% of megestrol acetate, about 15 to about 25% of polyethylene glycol; about 0.01 to about 0.04% of docusate sodium, and about 0.1 to about 0.3% of xanthan gum.

As part of the invention, there is also a method of forming an oral pharmaceutical composition in which a first portion of polyethylene glycol is combined with xanthan gum and water in a first vessel. A second portion of polyethylene glycol, docusate sodium and megestrol acetate is combined in a second vessel. The contents of the first vessel are then combined with the contents of the second vessel.

In another method as part of the invention, an oral pharmaceutical composition is formed by combining a first portion of polyethylene glycol, a first portion of water, docusate sodium and megestrol acetate in a first vessel. Xanthan gum, a second portion of water and a second portion of polyethylene glycol are combined in a second vessel. The contents of the first vessel are then combined with the contents of the second vessel.

Additional advantages and features of the present invention will become more readily apparent from the following detailed description which illustrates various embodiments of the invention.

DETAILED DESCRIPTION

The pharmaceutical composition of the invention is described as a flocculated aqueous suspension. A suspension is one in which solid particles of one or more active substances are suspended within a liquid medium. The liquid medium may contain various excipients, especially one or more wetting/dispersing agents and suspending agents. These excipients maintain the active in combinations or aggregations of suspended particles known as "floccules" or "flocs" within the suspension.

The composition of the invention is also described as being "stable". A stable suspension is one which can be redispersed or resuspended with light to moderate shaking throughout its shelf-life, thereby resisting caking or sedimentation. In addition, a stable suspension is one which resists changes in floccule particle size and distribution, the suspended active agent is not substantially degraded, nor is its bioavailability substantially affected over the course of its shelf life. The composition of the invention according to the embodiments hereinafter described should be stable, i.e., have a shelf-life of at least about two to about three months, preferably at least about 1 year, and more preferably at least about 18 months. It is especially desirable that the formulation be stable for at least about 2 to about 3 years, or even longer. Storage stability is typically measured with respect to ambient relative humidity, which is generally within the range of about 50% to about 80%, as well as temperature, which is typically within the range of about 25° C. to about 40° C.

In general, the aqueous pharmaceutical suspensions in accordance with the present invention will include an amount of at least one water-insoluble, pharmaceutically active agent which is sufficient to treat a mammal in need of treatment with the active. As used herein, the terms "water-insoluble" and "insoluble" refer to those substances which are insoluble, practically insoluble, or only slightly or sparingly soluble in aqueous media as those terms are described in the United States Pharmacopeia; Remington's Pharmaceutical Sciences, 18$^{th}$ edition published by Mack Publishing Company.

The pharmaceutical active utilized in the invention is preferably micronized or pulverized so that it has a "dry" mean particle diameter less than or equal to about 20 microns. Preferably, the mean particle diameter of the active substance alone will be within the range of about 1 micron to about 10 microns.

A non-exhaustive listing of suitable pharmaceutical actives from which the water insoluble active ingredient may be chosen include anti-cancer agents, antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasoditators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, antiemetics, anti-nauseants, anti-convulsants, neuromuscular drugs, hyper- and hypoglycemic agents, thyroid and antithyroid preparation, diuretics, antispasmodics, uterine relaxants, mineral and nutritional additives, antiobesity drugs, anabolic drugs, erythropoietic drugs, antiasthimatics, cough suppressants, mucolytics, anti-uricemic drugs, antiviral drugs and mixtures thereof.

Of the foregoing, anti-anorexia, cachexia compounds are particularly preferred. Especially desirable is megestrol acetate. Megestrol acetate is the generic name for 17-α-acyloxy-6-methylpregna-4,6diene-3,20-dione. Megestrol acetate in oral suspension form has now been indicated for use as an appetite stimulant, particularly for those suffering from "wasting" afflictions as a result of cancer, or diseases of the immune system such as AIDS. Megestrol acetate is insoluble in water, and exhibits a considerable degree of hydrophobicity.

The amount of pharmaceutical active used in the invention will depend on various factors, including the sex, age, weight, general health and condition of the patient and the type of drug and suspension. As a general rule, from about 0.1% to about 25% by weight of at least one substantial water-insoluble pharmaceutical active agent will be used (the weight percentage for the active agent is provided herein on a weight to volume, or w/v basis, and unless otherwise stated, all other weight percentages provided herein are on a weight to weight, or w/w basis). It is possible, however, depending on the nature of the dosage form, the active(s), and the indication(s), to create suspensions in accordance with the present invention that have greater than about 20% or less than about 0.1% of the active substance.

More preferably, the amount of insoluble active agent included in the suspensions of the present invention will range from about 0.5% to about 10%. Suspensions containing about 1% to about 8% of the active are even more preferred, with amounts within the range of about 2% to about 6% being most preferred. Especially desirable is a concentration level of about 4% of the active substance. Megestrol acetate utilized at about 4% is particularly preferred for use herein.

The flocculated suspensions in accordance with the present invention are principally prepared by combining the active substance with at least one wetting agent and at least one water-soluble polymer. The wetting agent acts as a vehicle to reduce the surface tension between the aqueous media and the insoluble active, thereby facilitating the active's maintenance in the aqueous media. The wetting agent may be chosen from available compounds known in the art. These can include, for example, sorbitan fatty acid esters, polyoxyethylene sorbitan fatty acid esters (TWEEN®), polyoxyethylene fatty acid esters, polyoxyethylene-polyoxypropylene copolymers and block copolymers. The wetting agent may also be chosen from the broad classes of surfactants, including nonionic, cationic, anionic, and zwitterionic surfactants known in the industry, some of which may overlap with those compounds mentioned above. Docusate sodium, polysorbate, e.g. polysorbate 80, and polyoxyethylene (40) stearate are especially useful, either alone or in combination, as wetting agents in the composition of the invention.

A particularly preferred wetting agent for use with the present invention is docusate sodium. Docusate sodium is known chemically as bis(2-ethylhexyl) sodium sulfosuccinate, and also as dioctyl sodium sulfosuccinate and sulfo-butanedioic acid 1,4-bis(2-ethylhexyl) ester, sodium salt. Other suitable docusate compounds and their salts are also within the scope of the invention. Docusate sodium is described as an anionic surfactant which is a white or almost white, wax-like, bitter tasting, plastic solid with a characteristic octanol-like odor. It is hygroscopic and usually available in the form of pellets, flakes or rolls of tissue-thin material. It has now been discovered that the use of docusate sodium, preferably in amounts of about 0.04% or less, results in stable and resuspendable flocculated suspensions. Moreover, it has also been found that decreasing the concentration of the wetting agent used in conjunction with the active substance to less than about 0.04%, it is further possible to actually improve flocculation overall. This in turn has further resulted in a noticeable increase in the size of the resulting floccules as well.

A preferred concentration of the wetting agent(s) in the composition of the invention is within the range of about 0.001% to less than about 2%. More desirably, the amount of wetting agent(s) will be in the range of about 0.005% to about 1%, with a range of about 0.01 to about 0.04% being preferred, and about 0.01 to about 0.03% being more preferred. When docusate sodium is utilized as the wetting agent, an amount of about 0.005%, preferably about 0.01%, to less than or equal to about 0.04% is highly desirable. More preferably, docusate sodium may be utilized in amounts of about 0.01% to about 0.025%, or desirably within the range of about 0.01% to about 0.02%. However, the invention is also intended to include other wetting agents and concomitant amounts thereof in which flocculation overall is achieved, and in particularly preferred embodiments floccule size is actually controlled by increasing or decreasing the concentration of the wetting agent within a certain range. Increased floccule size as a result of using docusate sodium, for example, within the described ranges has the effect of slowing the absorption of the active in many applications. While not wishing to be bound by theory, this perhaps is due to a decrease in the surface area of the active exposed to the mucosal surfaces of the stomach and gastrointestinal tract of the individual treated with the compositions of the invention.

The size or diameter of the floccules is believed to determine the rate of absorption of the active substance, and thus the therapeutic concentration in the bloodstream as measured against time. Larger flocs tend to expose less surface area of the active drug particles to contact the mucosal surfaces than do smaller flocs. Consequently, with larger flocs there is a lower rate of absorption of the active. Larger flocs are therefore typically desired in applications where it is important that the active substance not be absorbed too readily, i.e., not be in a state where it can be absorbed too quickly by the body. Smaller flocs are generally desired where the rate of absorption is to be accelerated. At the same time, floc size also impacts upon the dosage form in terms of the rate of sedimentation and ease of resuspendability, including the tendency to avoid precipitation in the G.I. tract. Consequently, in a preferred embodiment, the invention provides for the advantageous ability to control floc size so as to provide an optimal balance of several factors contributing to overall pharmaceutical elegance and utility.

It is generally desirable that the floccules in the aqueous suspension composition of the invention have a mean floc size diameter (<90%) up to at least about 12 microns, preferably up to at least about 21 microns, and more preferably up to at least about 23 microns. Stated another way, preferably up to 90% of the flocculated particles in the final formulation should be measured at up to a mean floc size diameter of at least about 12 microns, preferably up to at least about 21 microns, and more preferably up to at least about 23 microns, and even more preferably up to at least about 28 microns. Most preferably, the aqueous suspension will contain flocs whose mean floc size diameter (<90%) is as much as about 50 microns, or even more. ("Mean floc size diameter" is to be distinguished from the term "mean particle size diameter", which as used herein, refers to the diameter of the unagglomerated active particle.) (Example 10 below provides a suitable, non-limiting method for determining floccule size.)

Other preferred wetting agents along with suitable concentration ranges include the following: polysorbate, preferably polysorbate 80, in amounts equal to or greater than about 0.02%, more desirably equal to or greater than about 0.03% and less than about 0.1%; polyoxyethylene sorbitan fatty acid esters, preferably polyoxyethylene stearate, in amounts of about 0.0005 to about 1%, more preferably about 0.0005 to about 0.50%, more desirably about 0.03 to about 0.2%, and even more preferably about 0.03 to about 0.1%; and ethylene oxide-propylene oxide (EO-PO) copolymers and block copolymers, e.g. PLURONIC® F127, in amounts of about 0.0001 to 1.5%, more preferably about 0.001 to about 0.5%. In certain embodiments, docusate sodium (in amounts as heretofore described) together with polysorbate in the above amounts can be a highly suitable combination of wetting agents.

Further included as part of the composition of the invention is at least one suspending agent. Preferably, the suspending agent is a water-soluble polymer. The suspending agent, e.g. water-soluble polymer acts to maintain the wetted particles of the active substance(s) in homogeneous suspension. In this regard, certain nonionic polymeric compounds are desirable. These compounds can include certain classes of alkylcelluloses and alkylalkylcelluloses. Other compounds which are especially desirable include polyhydric alcohols. Of these, the alkylene polyols and polyalkylene polyols are preferred. Particularly preferred are propylene glycol, dipropylene glycol, polypropylene glycol, polyethylene glycol (PEG), sorbitol and glycerol. Polyethylene glycol is especially useful as the water-soluble polymer for use as part of the invention. In this regard, polyethylene glycol available from industry sources as PEG 200, 300, 400, 540 Blend, 600, Methoxy 750, 1450, 3350, and 8000 is preferred. Of these, PEG 1450 is especially preferred. Other suitable polyethylene glycols include those having a molecular weight (MW) within the range of about 200 to about 5,000. It is preferred, however, not to utilize polyethylene glycol together with polysorbate in the same formulation. In other embodiments, it may also be preferable not to utilize polyethylene glycol together with one or more EO-PO copolymers or block copolymers.

The concentration of the water-soluble polymer as part of the invention is generally greater than about 5% and less than about 50%. More desirably, amounts equal to or greater than about 10% are more preferred. Especially preferred is a concentration of water-soluble polymer within the range of about 15% to about 25%, with about 20% often being highly suitable.

In addition to the foregoing wetting agent(s) and water-soluble polymer(s), the flocculated suspension composition of the invention also desirably contains a second suspending agent. The second suspending agent is preferably a water-soluble hydrocolloid material. Like the water-soluble polymer described above, the hydrocolloid material further acts to suspend the active substance in the aqueous media. When both are utilized in the composition, the water-soluble polymer may be referred to as the first suspending agent, while the hydrocolloid material may be referred to as the second suspending agent. The hydrocolloid material is generally selected from available food-grade vegetable and animal sources. It is desirable that this material possess emulsifying and/or thickening properties. In this regard, pharmaceutically acceptable gums and gelatins are preferred. Of these, gums are especially desirable. Gums include, for example, guar gum, carrageenan, gum arabic and xanthan gum. Xanthan gum is particularly desirable for use with active substances such as megestrol acetate.

The hydrocolloid material is preferably utilized at concentration levels of about 0.05% to about 0.5%. More preferably, amounts within the range of about 0.1% to about 0.3% are used. A concentration of about 0.2% for the hydrocolloid material is even more desirable.

In addition to the components just described, the aqueous suspensions in accordance with the present invention may also contain a number of other ingredients. Sweeteners may be utilized as part of the composition to enhance the organoleptic properties of the suspension and to function as taste-masking agents. They may also be chosen to enhance the stability and/or viscosity of the final formulation. The preferred sweetener is sucrose and more preferably, sucrose syrup. Other suitable sweeteners can include, without limitation, saccharide material, and in particular, mono-, di-, tri- and oligosaccharides. Representative examples include glucose and fructose. Other examples of suitable sweeteners include the polyhydric alcohols, which are commonly used as sweeteners and include sorbitol, mannitol, or xylitol. Synthetic sweeteners such as sucralose, acesulfame, and aspartame may also be utilized.

The amount of sweetener used in accordance with the present invention can vary based on a number of factors. If the active is particularly bad-tasting, then more sweetener may be used. Generally, the amount of sweetener will range from about 0.5 to about 40%. Preferably, the amount used will be within the range of about 1 to about 20%, with about 2 to about 10% being particularly preferred. An especially desirable embodiment of the present invention will have about 7.6% of sweetener when the active ingredient is megestrol acetate.

Flavorants or flavors may also be used to enhance the organoleptic qualities of the final composition, preferably in synergistic effect with the just described sweetener(s). Any conventional, approved flavorants may be chosen so long as they do not materially affect the physical or chemical attributes of the active or of the resulting suspension. Both natural and synthetic flavorants are contemplated for use herein. Flavorants can therefore include vanilla, strawberry, cherry, grape, lemon, lime, orange, peppermint, spearmint, cinnamon, and any desired combination thereof. Flavorants will typically be added in amounts of from about 0.005% to about 20%, with about 0.01% to about 5% being especially desirable.

One or more antimicrobial agents or preservatives may also be used to form the aqueous flocculated suspension. Such agents can include, for example, the parabens such as methyl, propyl and butyl paraben, as well as compounds such as sodium benzoate, potassium sorbate, and sodium propionate, to name just a few. Sodium benzoate is particularly preferred. The antimicrobial agent should preferably not interfere with the floccules in the suspension, should be water-soluble, and should not adversely affect the taste or the pH of the final composition. The amount chosen can vary somewhat within a given range. A range of about 0.01% to about 1% is often desirable. Even more preferred is about 0.05 to about 0.5%.

pH modifiers or buffers may also be used to maintain the pH of the final composition within a certain desired range. pH often has a substantial effect on stability, and so the pH chosen should enhance stability of the formulation overall. Thus, the pH modifiers used in accordance with the present invention may be any pharmaceutical grade acid or base which is capable of maintaining the pH within an acceptable range. pH modifiers are generally used within the range of about 0.005 to about 1%, with about 0.01 to about 0.5% being more preferred. To acidify the final formulation, a combination of a weak acid and the salt of a weak acid may be chosen. In this regard, citric acid is particularly useful. Sodium citrate is also desirable. A combination of citric acid and sodium citrate is especially preferred. In addition, any combination of the previously mentioned antimicrobial agents/preservatives together with pH modifiers/buffers which yield a generally suitable ionic strength and pH, and which are pharmaceutically compatible, are suitable for use herein. The functions of an antimicrobial agent and a pH modifier can be obtained through the use of, for example, a mixture of sodium benzoate and citric acid with sodium citrate.

In addition to the foregoing components, the composition of the invention may also contain additional excipients. For example, humectants or other similar types of wetting agents may be used. Of these, glycerin is often desirable. FDA-approved colorants may also be chosen to make the formulation more visually palatable. Other viscosity modifiers may also be chosen. These optional ingredients, when included, will generally comprise about 0.01 to about 10% of the aqueous suspension. More desirably, they will comprise about 0.05 to about 0.5%.

The remainder of the compositions according to the invention is preferably water, but may be other potable liquid(s). The potable liquid is utilized in conjunction with the foregoing components so as to provide up to about 100% of the total composition.

Compositions according to the invention may be prepared by any suitable procedure. The following illustrative procedures may be utilized and are often preferred. According to a "two pot" process, a large proportion of a water-soluble polymer (e.g., polyethylene glycol 1450) is first melted. Upon melting, a hydrocolloid material (e.g., xanthan gum) is added and mixed until thoroughly dispersed in the melted polymer. This combination is then added (slowly) to the purified water under mixing. The resultant batch is then mixed for about an hour to ensure complete hydration of the hydrocolloid matter. Next, one or more preservatives (e.g., sodium benzoate) and pH modifiers (e.g., citric acid and sodium citrate) are added to the batch and the mixture is cooled to about 25–30° C. with mixing. One or more sweeteners (e.g., sucrose syrup) are then added with mixing. Batch weight is then adjusted, if desired, using purified water. The resultant mixture is referred to as Phase I. In another vessel, the remainder of the water-soluble polymer is added to hot purified water (70–75° C.) under agitation (high shear mixing). The wetting agent (e.g., docusate sodium) is then added to this batch and thoroughly admixed. The active (e.g., megestrol acetate) is then admixed into this batch under high shear. The resultant admixture is referred to as Phase II. Phase I is then added to Phase II under mixing and pressure (about 7–10 psi). The flavorants (e.g., lemon-mint) are then admixed into Phase II as well to produce the final formulation. If need be, formulation weight may be adjusted using purified water.

In another version of the "two pot" process described above, a large proportion of the water-soluble polymer, which has been melted or heated, is then combined with suitable amounts of water and the wetting agent is dissolved therein. The solution is then cooled (~25° C.), and the active substance is then added under low or high shear mixing conditions. In a separate container, the hydrocolloid material is prepared with suitable amounts of hot water (65–70° C.) and the remainder of the water-soluble polymer to form a liquid admixture. The remaining flavorants and excipients are then added and the resultant mixture may then be strained to remove any undissolved ingredients. This mixture is then combined with the mixture containing the active substance. The resultant admixture is thoroughly stirred and then passed through a mill. The resultant composition is an aqueous flocculated suspension.

In another embodiment of the invention, a "single pot" method of manufacture may be utilized. Hot purified water (70–75° C.) is transferred to a large pressure vessel. Using a hose and vacuum, a hydrocolloid material (e.g., xanthan gum) is preferably added from the bottom of the vessel. High shear mixing is then used to thoroughly hydrate the hydrocolloid material. This mixture then becomes the main phase. While maintaining the temperature of the batch at between about 60–70° C., a water-soluble polymer (e.g., polyethylene glycol 1450) is added to the main phase preferably from the top of the vessel. High shear agitation again is utilized to thoroughly mix all constituents. The temperature of the batch is then maintained to within 55–75° C., and a wetting agent (e.g., docusate sodium) together with any remaining excipients (e.g., preservatives, pH modifiers) are combined under vacuum until all solids are thoroughly dissolved. The mixture is then cooled to between about 25–30° C. while mixing continues. The active (e.g., megestrol acetate) is then added under vacuum and thoroughly mixed into the main phase to ensure that a good dispersion is obtained. Flavorants are then added and mixing continues until a good admixture is obtained. Batch weight is then adjusted, if desired, using purified water.

In yet another embodiment of the invention, the water-soluble polymer, wetting agent, hydrocolloid material, remaining excipients, and a suitable amount of water are combined with stirring (low or high shear) to thoroughly admix all ingredients. This admixture may be strained or screened. The active substance is then added to this admixture, and is thoroughly dispersed. The resultant mixture is then strained or passed through a colloid mill to yield the aqueous flocculated suspension of the invention. Other means of preparation in addition to any of the foregoing may also be effected by the skilled artisan.

The compositions according to the various embodiments of the invention may be orally administered to a mammal according to a dosing schedule prescribed by an appropriate health official. In a preferred embodiment, the composition is an oral suspension containing pharmaceutically acceptable amounts of megestrol acetate which is suitable for use in humans.

The following examples are intended to highlight certain embodiments of the invention, but should not be construed as limiting the scope thereof.

EXAMPLE 1

In this example, an aqueous flocculated suspension of megestrol acetate was prepared having the components set forth in TABLE 1 below:

TABLE 1

| Ingredient Name | Percentage by Weight |
| --- | --- |
| Megestrol Acetate | 40 mg/mL* |
| Docusate Sodium | 0.02 |
| Xanthan Gum | 0.2 |
| Polyethylene Glycol 1450 | 20.0 |
| Sodium Benzoate | 0.188 |
| Citric Acid | 0.244 |
| Sodium Citrate | 0.015 |
| Sucrose Syrup | 7.6 |
| Artificial Lemon-Mint Flavor | 0.045 |
| Purified Water | QS to 100% |

*Weight/Volume

The composition of TABLE 1 was found to exhibit excellent flocculation, stability, and resuspendability. The formulation readily dispersed with light shaking. Substantially no caking or sedimentation was observed.

EXAMPLE 2

In this example, an aqueous flocculated suspension of megestrol acetate was prepared having the same components and weight percentages as set forth in EXAMPLE 1, with the exception that the docusate sodium was utilized at a concentration of 0.01%. TABLE 2 sets forth the measured floc size in the resultant formulation:

TABLE 2

| Formulation | Mean Floc Size Diameter (Microns) | | |
| --- | --- | --- | --- |
| | D(10%) | D(50%) | D(90%) |
| Docusate Sodium @ 0.01% w/w | 7 | 17 | 28 |

EXAMPLE 3

In this example, an aqueous flocculated suspension of megestrol acetate was prepared having the same components and weight percentages as set forth in EXAMPLE 1, with the exception that the docusate sodium was utilized at a concentration of 0.04%. TABLE 3 sets forth the measured floc size in the resultant formulation:

TABLE 3

| Formulation | Mean Floc Size Diameter (Microns) | | |
| --- | --- | --- | --- |
| | D(10%) | D(50%) | D(90%) |
| Docusate Sodium @ 0.04% w/w | 2 | 12 | 21 |

As can be seen from TABLES 2 and 3, the floc size increases as the concentration of the surfactant docusate sodium is decreased from 0.04% to 0.01%.

EXAMPLE 4

In this example, an aqueous flocculated suspension of megestrol acetate was prepared having the same components and weight percentages as set forth in EXAMPLE 1, with the exception that polyoxyethylene (40) stearate was utilized at a concentration of 0.1% in place of docusate sodium.

EXAMPLE 5

In this example, an aqueous flocculated suspension of megestrol acetate was prepared having the same components and weight percentages as set forth in EXAMPLE 1, with the exception that polyoxyethylene (40) stearate was utilized at a concentration of 0.5% in place of docusate sodium.

EXAMPLE 6

The following alternative formulations of flocculated suspensions were prepared using the formulation of EXAMPLE 1, with the exception that in place of docusate sodium at 0.02%, the surfactants A) through D) at the concentrations noted were utilized. The following formulations also utilized 0.091% of lemon-lime flavor:

TABLE 4

| Wetting Agent | % by WT. |
| --- | --- |
| A.) Polyoxyethylene (40) Stearate (MYRJ 52)(from Example 4) | 0.1 |
| B.) Polyoxyethylene (40) Stearate (MYRJ 52)(from Example 5) | 0.5 |
| C) Docusate Sodium | 0.04 |
| D) Polysorbate 80 | 0.03 |

Formulations A) and B) were completely resuspendable with light shaking for 30 seconds after 12 months storage at 25° C. and 60% relative humidity (RH). Formulation C) was completely resuspendable with light shaking for 10 seconds after 12 months storage at 25° C. and 60% RH, while Formulation D) was completely resuspendable with light shaking for 20 seconds after 12 months storage at 25° C. and 60% RH.

Based at least in part on the extent of flocculation, the following formulations were chosen for further testing and development:

Polyoxyethylene (40) Stearate (MYRJ 52) @ 0.1% by wt.
Docusate Sodium @ 0.04% by wt.
Polysorbate 80 @ 0.03% by wt.

Batches of the foregoing were prepared at 500 kg batch size using a "single pot" manufacturing procedure, placed on stability and evaluated for particle size as part of full release testing. TABLE 5A provides mean particle size data, while TABLE SB provides mean floc size data (MYRJ 52 was not tested in TABLE 5B):

TABLE 5A

| Formulation Description | Mean Particle Size Diameters (microns) | | |
|---|---|---|---|
| | 10% < | 50% < | 90% < |
| MYRJ 52 (0.1% by wt.) | 1 | 4 | 11 |
| Docusate Sodium (0.04% by wt.) | 1 | 7 | 13 |
| Polysorbate 80 (0.03% by wt.) | 1 | 5 | 11 |

TABLE 5B

| Formulation Description | Mean Floc Size Diameters (microns) | | |
|---|---|---|---|
| | 10% < | 50% < | 90% < |
| Docusate Sodium (0.04% by wt.) | 2 | 12 | 21 |
| Polysorbate 80 (0.03% by wt.) | 1 | 6 | 12 |

In Examples 7–9, the formulation from TABLE 5 containing 0.04% docusate sodium was further evaluated to determine the effects, if any, of ionic strength, manufacturing process, and docusate sodium concentration on floccule size.

EXAMPLE 7

(Ionic Strength)

The effect of increasing the ionic strength was evaluated by varying the level of citric acid used in the formulation. There was substantially no change in floc size or viscosity.

EXAMPLE 8

(Manufacturing Process)

The formulation was manufactured using the "one pot" and the "two pot" process, as described above. No difference in floc size results were observed for this particular formulation.

EXAMPLE 9

(Docusate Sodium Concentration)

Formulations were prepared (2 kg. batch size) by reducing the amount of docusate sodium from 0.04% to 0.025%, 0.02% and 0.01%. Microscopic evaluation of the formulations indicated that as the level of docusate sodium was decreased to 0.01% there was an increase in the extent of flocculation. Results are tabulated in TABLE 6 according to the manufacturing method, "one pot" or "two pot," where indicated. At 0.01% docusate sodium, there was an increase in floccule size obtained when the two-pot manufacturing process was used compared to the one-pot process:

TABLE 6

| | Docusate Sodium | Mean Floc Size Diameter (Microns) | | |
|---|---|---|---|---|
| Description of Process | % by wt. | 10% < | 50% < | 90% < |
| 2-Pot Process | 0.04 | 2 | 13 | 22 |
| 1-Pot Process | | 2 | 13 | 23 |
| 2-Pot Process | 0.025 | 5 | 14 | 24 |
| 2-Pot Process | 0.02 | 6 | 14 | 24 |
| 2-Pot Process | 0.01 | 6 | 16 | 26 |
| 1-Pot Process | | 3 | 13 | 23 |

Pilot clinical trials were conducted using the formulations corresponding to the "one pot" process (0.01% and 0.04% docusate sodium) and the "two pot" process (0.01% docusate sodium), which indicated that the 0.01%—"two-pot" formulation was particularly well suited for further clinical evaluation.

EXAMPLE 10

(Method for the Determination of Floccule Size)

This example provides a suitable method for measuring the size of flocs in a liquid suspension. Equipment needed includes a Malvern Mastersizer X or equivalent, a 100 mm lens, a mixed cell adapter, and scintillation vials (20 mL) or equivalent. A sample cell is filled and mixed with deaerated purified water without incorporating air. 1.0 gram of the sample suspension is then added to a vial, and its weight is adjusted using 10.0 grams of the deaerated purified water. The vial is then covered and gently shaken until uniform. The suspension is then transferred to the sample cell using a dropper to obtain an obscuration level of about 15–30%. The sample cell is then mixed for about 2 minutes before taking a measurement. At least two readings, and preferably no more than three per sample, and then recorded and reported as 10%, 50% and 90% undersize. At least two sample readings should be within 10% of each other in order to be acceptable. Next, two more samples (for a total of three sample preparations) are prepared and read as described above, and the average of six readings is then recorded (rounded up to the next whole number).

EXAMPLE 11

Stability studies were conducted using the formulation containing 0.04% docusate sodium. Various samples of the composition were stored for 1 week, 2 weeks, 1 month, 6 weeks, 2 months, and 3 months, respectively, at 25° C., 40° C. and 50° C., respectively at ambient humidity. All were resuspendable at all times upon light shaking for about 30 seconds or less.

EXAMPLE 12

Stability studies were conducted as in Example 11, but using the formulation containing 0.1% Polyoxyethylene (40) Stearate (MYRJ 52) in lieu of docusate sodium. Various samples of the composition were stored for 1 week, 2 weeks, 1 month, 2 months, and 3 months, respectively, at 25° C., 40° C. and 50° C., respectively at ambient humidity. All were resuspendable at all times upon light shaking for about 30 seconds or less.

EXAMPLE 13

Stability studies were conducted as in Example 12, but using the formulation containing 0.5% Polyoxyethylene (40)

Stearate (MYRJ 52). Various samples of the composition were stored for 1 week, 2 weeks, 1 month, 2 months, and 3 months, respectively, at 25° C., 40° C. and 50° C., respectively at ambient humidity. All were resuspendable upon light shaking at all times for about 30 seconds or less.

EXAMPLE 14

A more detailed stability analysis was undertaken of the formulation using docusate sodium at 0.04% from Table 5 in Example 6. The results are shown in TABLE 7 below:

TABLE 7

| Analysis | Specifications | Initial | 1 month (40° C./75% RH) | 2 month (40° C./75% RH) | 3 month (40° C./75% RH) | 3 month (25° C./60% RH) | 6 month (25° C./60% RH) | 9 month (25° C./60% RH) |
|---|---|---|---|---|---|---|---|---|
| Megestrol Acetate | 40 mg/mL | 98.9% | 99.7% | 99.6% | 98.8% | 99.2% | 97.5% (U) 98.3% (I) | 98.4% (U) 98.0% (I) |
| Particle Size | TBD | 90% < 13 um 50% < 7 um 10% < 1 um | 90% < 14 um 50% < 6 um 10% < 1 um | 90% < 14 um 50% < 6 um 10% < 1 um | 90% < 16 um 50% < 8 um 10% < 1 um | 90% < 16 um 50% < 8 um 10% < 1 um | U: 90% < 9 I: 90% < 12 U: 50% < 4 I: 50% < 6 U/I: 10% < 1 | U: 90% < 15 I: 90% < 16 U: 50% < 8 I: 50% < 9 U/I: 10% < 1 |
| pH | 3.5–5.5 | 4.1 | 4.0 | 4.0 | 3.9 | 4.1 | (U/I:4.1) | (u/I):4.0 |
| Appearance | White to off-white suspension | White suspension | White suspension | White suspension | White suspension | White suspension | (U/I) White suspension | (U/I) White suspension |
| Viscosity (cps) | 75–300 | 175 | 157 | 152 | 147 | 161 | (U) 178.5 (I) 177.0 | (U) 152 (I) 156 |

(U) = bottle upright
(I) = bottle inverted

EXAMPLE 15

Another detailed stability analysis was undertaken of the formulation using docusate sodium at 0.01% prepared according to a "two pot" manufacturing process. The results are shown in TABLE 8 below:

TABLE 8

| Analysis | Specifications | Initial | 1 month (40° C./75% RH) | 2 month (40° C./75% RH) | 3 month (40° C./75% RH) | 3 month (25° C./60% RH) |
|---|---|---|---|---|---|---|
| Megestrol Acetate | 40 mg/mL | Beg- 97.2% Mid-101.6% End-99.3% | 100.7% (U) 101.0% (I) | 95.8% (U) 100.0% (I) | 97.7% (U) 96.5% (I) | 98.5% (U) 98.0% (I) |
| Particle Size (U/I) (microns) | TBD | 90% < 15 um 50% < 8 um 10% < 1 um | 90% < 12 um 50% < 6 um 10% < 1 um | 90% < 16 um 50% < 9 um 10% < 1 um | 90% < 18 um 50% < 10 um 10% < 2 um | 90% < 17 um 50% < 10 um 10% < 1 um |
| PH (U/I) | 3.5–5.5 | 4.1 | 4.1 | 4.0 | 4.0 | 4.1 |
| Appearance | White to off-white suspension | White suspension | White suspension | White suspension | White suspension | White suspension |
| Viscosity (U/I)(cps) | 75–300 | 207 | 187 | 156 | 156 | 194 |

(U) = bottle upright
(I) = bottle inverted
(U/I) = average of bottle upright and bottle inverted values The foregoing description is illustrative of exemplary embodiments which achieve the objects, features and advantages of the present invention. It should be apparent that many changes, modifications, and substitutions may be made to the described embodiments without departing from the spirit or scope of the invention. The invention is not to be considered as limited by the foregoing description or embodiments, but is only limited by the construed scope of the appended claims.

What is claimed as new and desired to be protected by Letters Patent of the United States is:

1. A method for forming an aqueous flocculated suspension containing 40 mg/ml micronized megestrol acetate together with a wetting agent to form a stable, resuspendable flocculated suspension of megestrol acetate, comprising mixing the wetting agent with micronized megestrol acetate in an amount such that about 90% of the floccules of megestrol acetate in the suspension have a diameter of less than 12 to 50 microns, and wherein the flocculated suspension does not simultaneously contain polysorbate and polyethylene glycol.

2. The method of claim 1, wherein about 90% of the floccules have a diameter of less than 21 to 50 microns.

3. The method of claim 1, wherein about 90% of the floccules have a diameter of less than 23 to 50 microns.

4. The method of claim 1, wherein about 90% of the floccules have a diameter of less than 26 to 50 microns.

5. The method of claim 1, wherein about 90% of the floccules have a diameter of less than 28 to 50 microns.

6. The method of claim 1, wherein about 90% of the floccules have a diameter of less than 12 to 28 microns.

7. The method of claim 1, wherein about 50% of the floccules have a diameter of less than 17 microns.

8. The method of claim 1, wherein about 10% of the floccules have a diameter of less than 7 microns.

9. The method of claim 1, wherein the micronized megestrol acetate has a particle size wherein about 90% of the particles have a diameter of less than 20 microns.

10. The method of claim 1, wherein the micronized megestrol acetate has a particle size wherein about 90% of the particles have a diameter of less than 11 to 20 microns.

11. The method of claim 1, wherein the wetting agent is a polyoxyethylene wetting agent.

12. The method of claim 1, wherein the wetting agent is docusate sodium.

13. The method of claim 1, wherein the wetting agent is docusate sodium in an amount of about 0.01 to about 0.04% w/w.

14. The method of claim 1, wherein the wetting agent is docusate sodium in an amount of about 0.02% w/w.

15. The method of claim 1, further comprising mixing the megestrol acetate with one polyhydric alcohol component, a hydrocolloid component, and a buffer.

16. The method of claim 15, wherein the polyhydric alcohol component consists essentially of glycerol.

17. The method of claim 15, wherein the hydrocolloid component comprises a material selected from the group consisting of xanthan gum, hydroxypropyl cellulose, and carboxymethyl cellulose.

18. The method of claim 15, wherein the buffer is selected from the group consisting of sodium citrate and citric acid.

19. The method of claim 15, further comprising adding a preservative.

20. The method of claim 19, wherein the preservative is sodium benzoate.

21. The method of claim 15, wherein the hydrocolloid component is xanthan gum.

22. The method of claim 1, further comprising passing the suspension through an agitation means for dispersing the micronized megestrol acetate.

23. A method for forming an aqueous flocculated suspension containing 40 mg/ml micronized megestrol acetate together with a wetting agent to form a stable, resuspendable flocculated suspension of megestrol acetate, comprising mixing the wetting agent with micronized megestrol acetate in an amount such that about 50% of the floccules of megestrol acetate in the suspension have a diameter of less than 17 microns, and wherein die flocculated suspension does not simultaneously contain polysorbate and polyethylene glycol.

24. A method for forming an aqueous flocculated suspension containing 40 mg/ml micronized megestrol acetate together with a wetting agent to form a stable, resuspendable flocculated suspension of megestrol acetate, comprising mixing the wetting agent with micronized megestrol acetate in an amount such that about 10% of the floccules of megestrol acetate in the suspension have a diameter of less than 7 microns, and wherein the flocculated suspension does not simultaneously contain polysorbate and polyethylene glycol.

* * * * *